(12) United States Patent  
Padula

(10) Patent No.: US 8,262,590 B2  
(45) Date of Patent: Sep. 11, 2012

(54) GAIT/BALANCE ANALYZER

(76) Inventor: William V. Padula, Guilford, CT (US)

( * ) Notice: Subject to any disclaimer, the term of this patent is extended or adjusted under 35 U.S.C. 154(b) by 160 days.

(21) Appl. No.: 12/798,264

(22) Filed: Apr. 1, 2010

(65) Prior Publication Data

US 2010/0262046 A1     Oct. 14, 2010

Related U.S. Application Data

(60) Provisional application No. 61/212,089, filed on Apr. 7, 2009.

(51) Int. Cl.  
*A61B 5/11*     (2006.01)

(52) U.S. Cl. ........................................ 600/592; 600/595

(58) Field of Classification Search .................. 600/587, 600/592, 595

See application file for complete search history.

(56) References Cited

U.S. PATENT DOCUMENTS

| | | | | |
|---|---|---|---|---|
| 5,299,454 | A * | 4/1994 | Fuglewicz et al. | 73/172 |
| 6,231,527 | B1 * | 5/2001 | Sol | 600/595 |
| 2006/0264786 | A1 * | 11/2006 | Nashner | 600/595 |
| 2009/0137933 | A1 * | 5/2009 | Lieberman et al. | 600/595 |
| 2009/0240170 | A1 * | 9/2009 | Rowley et al. | 600/595 |
| 2010/0035727 | A1 * | 2/2010 | Brunner | 482/8 |

OTHER PUBLICATIONS

Dickstein et al. "Light touch and center of mass stability during treadmill locomotion," Gait and Posture 20 (2004) 41-47.*  
Basford et al. "An assessment of gait and balance deficits after traumatic brain injury," Arch Phys Med Rehabil vol. 84, Mar. 2003.*

* cited by examiner

*Primary Examiner* — Max Hindenburg  
*Assistant Examiner* — Michael C Stout  
(74) *Attorney, Agent, or Firm* — DLA Piper LLP (US)

(57) ABSTRACT

An apparatus for analyzing gait and balance to determine visual spatial distortion including a treadmill having a movable tread, at least a weight bearing sensor for measuring weight bearing pressure in right, left, front and rear directions provided under said tread and an analyzer for analyzing lean coupled to output of said weight bearing sensor.

5 Claims, 2 Drawing Sheets

GAIT/BALANCE ANALYZER

FIELD OF THE INVENTION

Apparatus and method for measuring neuro-optic distortion, particularly visuo-spatial distortion following a cerebrovascular accident and Post Trauma Vision Syndrome.

BACKGROUND OF THE INVENTION

Following a cerebrovascular accident (CVA), individuals initially tend to lean toward the side of the hemiparesis. A long-term effect of this condition has been termed Pusher Syndrome. It has been shown that there is a severely disturbed perception of body orientation unrelated to vestibular dysfunction (e.g. a sensorimotor mismatch without vestibular dysfunction affecting position sense). It has been suggested that it is caused by a disturbed representation of body-space orientation (e.g. spatial organization to maintain upright body position against gravity), in turn affecting leg-trunk orientation and causing a lean into the affected side and a 'push' away from the functional side. However, within the first few weeks many will develop compensations causing a tendency to lean away from the hemiparetic side. The assumption is that this phenomenon has a neurological cause related to the weakness of the paretic side. The significance of this trend is that the lean into the affected side (Pusher's Syndrome) and then the developed compensatory lean away from the affected side is due to a reorganization of information from sensorimotor systems in context with weakness from the paretic side.

In addition to leaning away from the paretic side following a CVA, it is also common to have a neglect of one's visuo-spatial awareness on the affected side. It has been reported that 60% of CVA patients had a unilateral neglect. Furthermore, spatial neglect will cause a postural imbalance, thereby causing weight-bearing asymmetry (e.g. inappropriate body-space orientation causing a lateral shift in perceived concept of upright posture against gravity). When persons exhibit neglect, not only do they miss seeing objects in the neglected field, but they will often twist and/or lean away from the affected visual field. The twisting or turning of their body will compromise the ability to maintain equal weight displacement between the lateral components of their body. Some individuals will torque their bodies to the extent that they are looking and turning their bodies 90 degrees or greater away from their centre or midline. This deviation in body position is a phenomenon that has been interpreted related to a lack of attentive awareness regarding a lateral aspect of the visual field. However, consideration that this phenomenon is due to mismatch between the spatial component of the visual process and sensorimotor information may offer greater insight as to its cause.

Rehabilitation following a CVA requires extensive physical and occupational therapy in an attempt to facilitate proprioceptive and spatial awareness on the affected side, through weight-bearing, to improve posture and balance. It has further been reported that of patients receiving appropriate rehabilitative care, 20% had an increased length of stay related to CVA associated perceptual spatial problems.

Prisms have been demonstrated to have a beneficial effect to improve visually guided action and perception as well as to affect-posture among patients with CVAs. has been. demonstrated improvement in daily life activities, such as postural balance and spatial orientation through the use of prism adaptation (e.g. the use of prisms to establish visual and sensorimotor awareness of neglected field). It has been also found that improvement in visuo-manual adaptation with prisms occurs, thereby reducing visuo-spatial neglect. This further suggests that the prisms may activate brain functions related to multi-sensory integration.

A prism is a wedge of optical media typically made from plastic, glass, or polycarbonate Prisms are traditionally prescribed in glasses to compensate for a deviation in eye alignment. However, yoked prisms, as used in this study are not for compensation but instead used to affect position sense and orientation to body space. A prism is shaped with an apex at the thin end and a base at the thick end of the prism. The angle of degree deviates a beam of light such that the image of an object will be shifted a centimeter (cm) per dioptre of prism at a distance of 1 meter (m). For example, five dioptres of prism deviates an image 5 cm at a 1 m distance. A prism shifts an image due to properties that compress space in one direction and expand space in another direction. Yoked prisms expand and compress space equally for both eyes. The expansion and compression of space through the use of yoked prisms becomes the rehabilitative utility to neutralize the sensorimotor distortion caused by mismatch between the affected (paretic) side and the non-affected side.

SUMMARY OF THE INVENTION

Therefore it is an object of the present invention to analyze the distortion in visuo-spatial dysfunctions (e.g. mismatch between visuo-spatial and sensorimotor information affecting position sense) related to hemiparesis and the effects of modifying these dysfunction through us of yoked prisms. Yoked prisms (i.e. two prisms introduced before the eyes with the base or thick ends of the prisms in the same direction) were used to counter the spatial distortion which can cause a shift in an individual's concept of egocentric midline (e.g. a preconscious organization through sensorimotor matching of the lateral and anterion-posterior axes related to perceived body centre for position sense).

To achieve this object in a dynamic environment, an apparatus including a tread mill with means for measuring the foot pressure at various points utilizing weight-bearing pressure sensitive walk plates provided under the tread and/or overhead supporting means is provided to measure the weight bearing pressure in the forward, rear, right and left directions. The measurements from the tread mill are supplied to an analyzing means for determining the amount of visual midline shift and thereby the number of dioptres needed for the yoke prisms in order to correct the shift.

BRIEF DESCRIPTION OF THE TABLES

Figure 2:
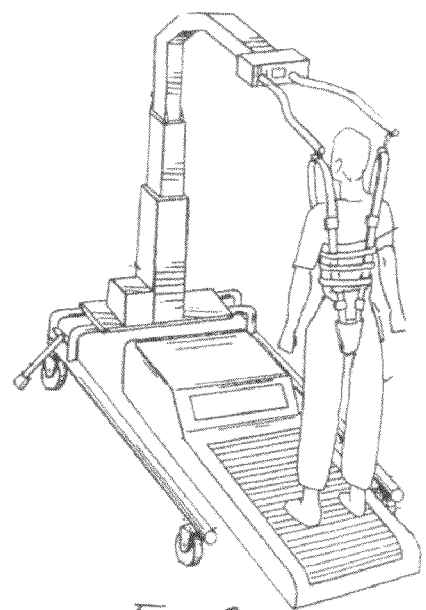
FIG. 2 is a treadmill with weight bearing pressure determining means included.

Table I. Demographic characteristics of experimental and control subjects.

Table II. Shifts in visual midline for all subjects.

Table III. Modification of VMS using yoked prisms. Table IV. Direction of lean or drift while ambulating. Table V. Effects of yoked prisms on direction of lean or drift while ambulating.

INCORPORATION BY REFERENCE

The entire contents of Provisional Application No. 61/212,089 is incorporated by reference herein.

DETAILED DESCRIPTION OF THE INVENTION

To explain the role of vision in affecting posture, balance, and midline development, vision is a bimodal processing system composed of both focal and ambient vision. The focal visual process is largely concerned with detail discrimination. This component of the visual process isolates on pieces and parts with limited ability to create relationships. It is analogous to seeing the 'trees' but not the 'forest', or as some persons with traumatic brain injury (TBI) describe, they can see a nose, a lip, and an ear but they cannot see a face. The process of focalization is a function of occipital cortical function. Focalization is supported by the ambient process which relates to spatial orientation (e.g. utilizing the framework of our visuo-spatial environment to match with sensorimotor information for body-space orientation). The ambient system comprises of up to 20% of the nerves emanating from both eyes. These nerve fibres relay axons to the midbrain where visual information is matched with kinaesthetic, proprioceptive, and vestibular sensorimotor information.

Ganglion cells from the retina can be traced from the optic nerve and chiasm to the optic tract where they reach three major destinations: (1) the lateral geniculate body for relay to the visual cortex, (2) the pretectal nucleus concerned with pupillary constriction, and (3) the superior colliculus where they merge with input from the sensorimotor system. The superior colliculus receives these nerve fibres from the optic tract through the superior brachium, from the occipital cortex via the optic radiations through the lateral geniculate body, and from the spino-tectal tract completing connections with the sensorimotor systems from the spinal cord and medulla. This interaction and matching of retinal and sensorimotor information provides the input for posture, balance, movement, and positional orientation.

Following this matching effect, a feed-forward mechanism communicates from the midbrain with the occipital cortex and many other areas of the brain to establish a spatial construct of visual domain as well as organization for other higher sensory and cognitive perceptual processes. For example, preconscious ambient and sensorimotor matching provides the spatial reference domain that becomes the base or platform for the awareness of higher cognitive processes such as seeing the detail, becoming aware of position sense, localizing a sound, anticipating change such as releasing from a point of visual fixation to another point of regard, or to accurately visually track a moving object.

It can be demonstrated that involvement of the superior colliculus in visual search tasks supports a dependency of superior colliculi activity on functions beyond oculomotor control and visual processing. A two-visual system model enables one to predict that cortical dorsal streaming mediates normal visual-guided actions, while ventral streaming deals with visual information that is memory-based. Spatial information from the ambient visual process, delivered by the superior colliculus, provides the binding format of the fusion process for integrating the images from the right and left eyes.

My research has demonstrated that dysfunction of the ambient visual process interferes with amplitudes of binocular visual evoked potentials. Post Trauma Vision Syndrome (PTVS) was the name given to describe the dysfunction of ambient visual processing yielding over-focalization on detail, which can compromise higher cognitive processing (e.g. perception, memory, executive skill, etc.) and binocular vision functions (e.g. ability to scan, track converge the eyes, accommodate, etc). It is also know that damage to the superior colliculus produces exotropia and diplopia. These binocular dysfunctions are common among TBI and similar to the characteristics and symptoms I have researched which documents that the binocular dysfunction is a result of interference with ambient visual processing at the level of the thalamus.

Dysfunction of the ambient visual process in relationship to mismatch between sensorimotor information also relates to concepts of visual midline organization (e.g. the preconscious ambient visual concept of the lateral and anterionposterior axes related to the perceived body centre for sense of position), whereby a simple test can determine shifts in an individual's concept of egocentric visual midline. It has been determined that pathological shift of the subjective midline will occur relative to left hemispatial neglect, and that treatment with yoked prisms demonstrated improvement or reduction in neglect.

In practice, the use of yoked prisms have been shown to counter the distortion of compression and expansion of visual space caused by a CVA. This can result in increased weight-bearing (e.g. realigning position sense and shifting weight more equally between affected and non-affected side) on the affected side by realigning internalized concepts of midline. For example, yoked prisms affect three-dimensional space. The base-end of the prisms will compress space in the lateral direction and expand space in the anterior/posterior direction. The apex-end of the prism will expand space in the lateral direction and compress space in the anterior/posterior direction. In turn, base-right or base-left yoked prisms will produce an equal compression and expansion of space for each eye thereby affecting the interpretation of space through ambient visual process matching with sensorimotor information.

Figure 1:
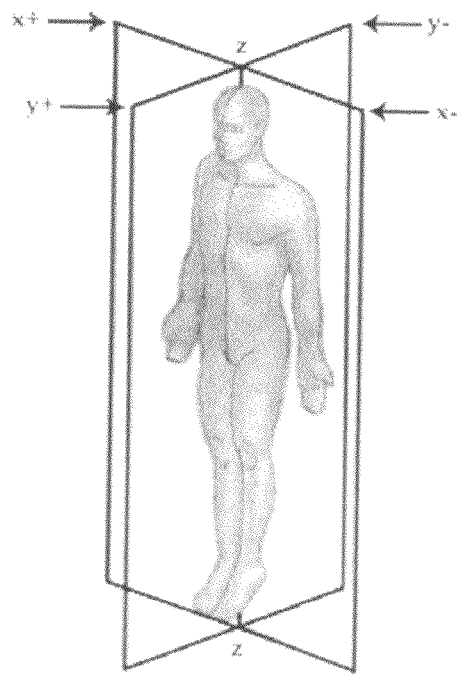
FIG. 1 is a graphical representation of ambient visuo-spatial volume affecting egocenter.
Figure 3:
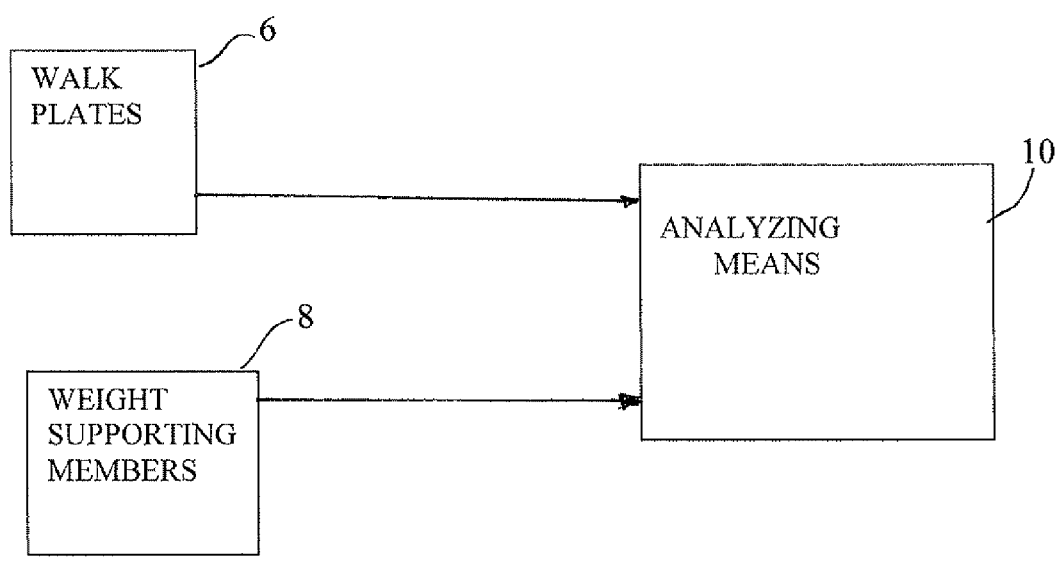
FIG. 3 is a block diagram of the present invention.

The concept of distortion of the ambient visual space/volume can be represented mathematically and graphically in FIG. 1.

The visuo-spatial volume is represented by axes x, y and z, and radius from the egocenter, r in FIG. 1. The concept of egocenter represents the relationship between the preconscious ambient and sensorimotor processes. The resulting compression and expansion of ambient visual space occurring as distortion is caused by a mismatch between ambient and sensorimotor information. This can be understood by changes in values of x+ and x− as well as y+ and y−. For the purposes of this model (z=r). The shift of the visuo-spatial egocenter affecting the concept of visual midline, and as a result, egocentric directionality, can be represented in equation 1 below:

$$\frac{x^2 + y^2 + z^2}{r^2} = 1 \qquad \text{Equation 1}$$

For example, if a subject in the control group demonstrated equality between the sum of the squared axes (i.e. $(x^+-x^-)^2$, $(y^+-y^-)^2$, $(z^+-z^-)^2$) and the radius from the physiological egocenter (i.e. $r^2$), then the left side of the equation will equal one. This in turn demonstrates that the spatial volume of x, y and z are equivalent and the visual egocenter (midline) is centred. Therefore, the subject shows no bias or lean in the lateral or anterior/posterior axis. However, if there is a lateral shift for a subject in the experimental group such that x− is greater that x+, x− will be greater than one. This inequality indicates a shift in visual egocenter due to unequal ambient spatial volume, thereby coinciding with the angle of lean.

The hypotheses being tested are: (1) that the shift in weight-bearing away from the hemiparetic side is due, at least in part, to a shift in the concept of visual midline; and, (2) that yoked prisms with the base of the prism positioned opposite to the shift of visual midline can effectively realign the concept of visual midline. Thus, postural orientation while ambulating is corrected to a state similar to pre-CVA. My study demonstrated (1) a correlation in direction of visual midline shift (VMS) to the side opposite the hemiparesis; (2) the influence of yoked prisms on realigning the visual midline; (3) the relationship of visual midline to postural orientation; and (4) the effectiveness of yoked prisms on influencing concepts of visual midline to affect posture.

Methods

Design

In the design of my study, consideration was given to a double-blind study. However, due to the thickness of the base-end and the spatial effect produced by the yoked prisms, masking of the placebo could not be insured. Therefore, each subject in the experimental group and control group was given a random assignment for use of a base-left or base-right yoked prism. The randomized assignment of the yoked prisms reduced the possibility of anticipation affecting outcome by the subject. A double-blinded study would not have reduced this anticipation and would have presented this confounding variable caused by the subject's awareness of using yoked prisms in contrast to the placebo.

Subjects

My study participants were either in an intervention group or a control group. Members for the intervention and control groups were seen in a clinical setting and chosen in a consecutive manner (sequential order of presentation) as each subject met the criteria for this study. In the intervention group, the mean age was 68 years (SD=6.75), and 50% of subjects were male. The mean age of the control group was 63 years (SD=6.12), and 60% were male. All subjects in this study met the following inclusion criteria: subjects were binocular (i.e. subjects with strabismus were not included in this study) with refractive correction equal to or less than +/−2.00 dioptres; subjects were ambulatory and able to communicate. No subjects had greater than a +/−0.50 dioptre anisometropia (unequal refractive power). No refractive correction was used during the testing, and no subject had scotomas so that there would not be any spatial disorientation due to field loss. There were thirty adults in the intervention group, all of whom had had a CVA. The occurrence of the CVA in the experimental group ranged from one year to three years. The thirty controls had no known neurological impairment. Seven females and 10 males were in the Right CVA group, with eight females and five males in the left CVA group. Other demographic relationships between the subjects in the experimental and control groups are displayed in table I.

Procedure

All subjects in both the experimental and control groups participated in all four aspects of testing. Testing conducted was part of a standard evaluation protocol developed and used in this clinical setting.

Visual Midline Shift

The initial step in the diagnosis of a subject with a VMS is qualitative (e.g. investigator observes tendency of the subject to lean) since it requires observation of postural alignment and behaviour, as well as a determination of the side of the CVA (right or left). Each subject was seated before a blank wall and asked to position his or her head directly forward. A 30 cm wand was held vertically 45 cm in front of the right shoulder. The subjects were asked to follow the wand with eye movements only and to state when the wand appeared to be directly in front of their nose. The wand was moved in front of each subject's facial plane in a horizontal pattern from the right shoulder toward the left shoulder at a speed of approximately 4 cm per second representing a subtended arc of approximately 70 degrees from the bridge of the nose of the subject. The test was then repeated by moving the wand from the left shoulder toward the right shoulder. Two responses (i.e. a response by the subject reporting the wand to be at the perceived alignment directly in front of their nose when the wand was first moved left to right, and then right to left) were recorded for each subject.

During this test the investigator was seated indiscriminately to the left or right side of the subject at approximately a 30 degree angle to the subject's chair. This was carried out in order to lessen any influence of the investigator's position on the subject's responses. A response by the subject reporting the perceived alignment of the wand with the centre of their nose but actually shifted away from their hemiparetic side indicates a shift in the subject's perceived visual midline away from the hemiparetic side. A response away from the hemiparetic side was scored 'positive' whereas a report of the wand aligned toward the hemiparetic side was scored 'negative'. For example, subjects who had experienced a right CVA and demonstrated a left hemiparesis scored positive if the response was to the subject's right of physical midline.

Yoked Prisms Affecting the Concept of Visual Midline

The test for visual midline shift was repeated with the subjects wearing a frame holding twelve dioptres of yoked prisms, initially with base-left and, subsequently, in the base-right position. The scores demonstrate the number of positive responses indicating a continued shift in the perception of visual midline away from physical midline. Each subject was tested with both prism configurations.

Postural Orientation

The subjects were observed individually to stand and walk 5 m forward, turn around, and return to the starting position without yoked prisms. Twenty-seven subjects in the intervention group utilized a cane or hemi-walker. A positive score represented a tendency to lean more than approximately 10 degrees from an erect position and/or drift away from the hemiparetic side. A lean of 10 degrees was chosen by the investigators because less than 10 degrees could be potentially due to sway. A lean of 10 degrees or greater was easily observed and was beyond variation in position due to normal movement.

The Influence of Yoked Prisms on Postural Orientation

Each subject was fitted with twelve dioptres of yoked prisms. The amount of prism was chosen because twelve dioptres has the effect of 12 degrees of spatial expansion and compression within the visual field. The spatial expansion and compression are a function of prism and are used to counter the effect of distortion and the resulting shift of visual midline in the ambient spatial field for subjects in the intervention group. Observations of each subject were made individually while standing then subsequently walking, as described in Part three: postural orientation. A 'positive' score was given if the subject continued to lean or drift away from the hemiparetic side. The 'positive' score related to the compression and relative expansion of spatial volume of equation 1 ($x=-x^-$) such that a 10 degree of lean of a subject that was 6 feet (ft) tall would equate to:

$$\frac{(6-4)^2 + (6-6)^2 + (6-6)^2}{6^2} = 0.111 \qquad \text{Equation 2}$$

Thus, for a person who is 6 ft tall, more than eleven prism dioptres are required to observe a correction of at least 10 degrees of lean. This could also be clarified as the egocenter experiencing approximately 2 ft of displacement in the x⁻-direction. Twelve dioptres of prism are chosen to remain consistent for all test subjects.

Data Analysis

We analysed visuo-spatial dysfunction related to hemiparesis in post-CVA subjects, and the effects of using yoked prisms to modify an individual's concept of visual midline. The test of proportions was used to compare the proportion of subjects with a positive VMS in each part of the method to a hypothetical proportion. We hypothesized that the following results would occur in the intervention group at a rate of 50%: subjects with a CVA would have a 'positive' VMS in order to correlate the VMS with the hemiparesis, subjects would have a tendency to lean or drift away from the hemiparetic side and, lastly, that use of appropriate yoked prisms would reduce the lean or drift as judged by observed postural changes. Based on the properties of the test of proportions, if subjects of the left CVA group or the right CVA group experienced 'positive' outcomes at a rate of 50%, or close to that rate with at least 95% confidence ($P<0.05$) then the results were statistically significant.

In contrast to the intervention group, the predicted results of the control group matched the null hypothesis. Yoked prisms should have no effect on correcting the VMS of control subjects since they are expected to have no VMS during the course of the trial. Therefore, a test of proportions is designed to show that compared to the intervention group's rate of 50% positive effect, the group of control subjects should not have any characteristics of VMS at statistically significant levels. These characteristics include an initial shift of the visual midline and related lean. Furthermore, descriptive statistics were used to characterize the effect of yoked prisms on control subjects.

Results

Confirmation of Visual Midline Shift

Table II shows the results of visual midline testing for right and left CVA subjects and compares those with positive shifts (perceived centre shifted away from the hemiparetic side) to those with negative shifts (toward the hemiparetic side), see table II.

Of subjects with a right CVA, 79% of the trials for these showed a positive response, indicating subjects' perceived VMS away from the hemiparetic side, and with perception of visual midline deviating to the right of physical midline ($P<0.001$; 95% confidence interval [CI], 0.66 to 0.93). A negative response or a VMS toward the hemiparetic side resulted in 21% of trials. This indicates a paradoxical shift of visual midline causing a push by the subject into the side of weakness. The paradoxical VMS may be a contributor to the effect observed in Pusher Syndrome.

For the subjects with a left CVA and right hemiparesis, 77% of trials resulted in a positive response with subjects demonstrating a perceived concept of visual midline to the left side, away from the hemiparesis ($P=0.001$; 95% CI, 0.61 to 0.93). There was a negative response in 23% of these trials.

In the control group, only 6% of trials showed a shift to the right and in only 1% of trials was there a shift to the left. The visual midline shift in the control group was not statistically significant ($P=0.31$; 95% CI, −0.031 to 0.098).

Placements of Yoked Prisms

Table III depicts the results of the use of yoked prisms on midline shifts by looking at how many positive shifts (leaning away from the hemiparesis) occurred while using the prisms.

When testing those subjects with a right CVA and left hemiparesis, use of appropriate base-left yoked prisms decreased the positive responses (i.e. VMS away from the hemiparetic side) by 85% ($P<0.001$; 95% CI, 0.73 to 0.97). However, the use of base-right yoked prisms in the right CVA group resulted in a decrease in positive responses of only 26%. For those with a left CVA and right hemiparesis when testing with base-left yoked prisms, there was a decrease of positive responses in 24%. Conversely, the left CVA group experienced a 77% decrease in positive VMS with base-right yoked prisms ($P=0.001$; 95% CI, 0.069 to 0.39).

The control group showed no bias to either base-left or base-right yoked prisms with 45% of trials showing a left shift with base-left yoked prisms, and 43% of trials showing a right shift with base-right yoked prisms. Due to the effect of the base-left and base-right prism neutralizing subjects' bias in the control group, there is no measure for statistical significance.

Looking for Lean

The postural orientation of the subjects as to observed lean or drift while ambulating without yoked prisms was analyzed. The results are shown in table IV.

Of subjects who had a right CVA, 94% developed either a lean or drift away from the hemiparetic side, or pdsitive lean, and only one subject leaned or drifted into the hemiparetic side, or negative lean ($P<0.001$; 95% CI, 0.83 to 1.0). Of the subjects with a left CVA, 77% leaned or drifted away from the hemiparetic side, and only 23% leaned or drifted towards it ($P=0.02$; 95% CI, 0.54 to 1.0).

In the control group 80% of the subjects showed no lean or drift. Members of the control group do not lean or drift frequently enough for there to be any correlation between posture and the absence or presence of a VMS ($P=0.14$; 95% CI, −0.023 to 0.16 for right lean, and $P=0.31$; 95% CI, −0.031 to 0.098 for left lean).

Correcting Lean

The use of yoked prisms for modifying the VMS to influence posture and balance during weight-bearing and ambulation was evaluated.

Table V shows that for right CVA subjects 82% showed improvement in weight-bearing with appropriate prisms ($P<0.001$; 95% CI, 0.64 to 1.0). Conversely, only 18% continued to lean away from the hemiparesis when fitted with base-left yoked prisms. For left CVA subjects, only 15% continued to lean away from the hemiparesis with base-right yoked prisms, while 85% showed an improvement in weight-bearing with base-left yoked prisms ($P<0.001$; 95% CI, 0.65 to 1.0). However, with base-left yoked prisms the abnormal lean into the hemiparesis persisted for most subjects.

In the control group, nearly half of the subjects leaned toward the base side of the yoked prisms. The data for this group demonstrate that both base-left and base-right yoked prisms will put control subjects off-balance.

Over the past several years visuo-spatial dysfunctions related to hemiparesis and the effects of modifying them with yoked prism has been observed. The effect of short-term prism adaptation on both visuo-spatial neglect and postural imbalances following right hemispherical damage has been documented. It has been determined that prism exposure evokes three kinds of adaptive or compensatory processes: postural adjustments involving visual capture and muscle potentiation, strategic control for recalibration of target position, and spatial realignment of various sensory motor reference frames.

Results of my research have confirmed the observations that most post-CVA subjects have a shift in the perceived concept of egocentric midline opposite the side of hemiparesis and that this shift can be clinically reduced and moved towards physical midline in the majority of cases through the use of yoked prisms. Of considerable clinical importance is the fact that we were also able to show that the lean or drift away from the hemiparetic side was consistent with the shift in the visual concept of egocentric midline and that in 80% or more of the subjects VMS could also be reduced with yoked prisms.

The characteristics of shift of perceived egocenter demonstrated by subjects in this study have been given the name Visual Midline Shift Syndrome (VMSS). Results of this study raise some important points that need to be considered clinically regarding the short and long-term rehabilitation needs of patients with VMSS. These results demonstrate that the visual process is dynamically involved in establishing a preconscious organization of visual midline relative to neurological changes occurring from a hemiparesis. The study also shows that this distortion in visuo-spatial processing produces a lean and/or drift away from the hemiparetic side. This will reinforces the inability to establish weight-bearing on the affected side. This distortion is a function of a relative compression and expansion of space through ambient spatial and sensorimotor preconscious mismatch that occurs following a neurological event such as a CVA.

Visuo-spatial neglect involves the lack of conscious awareness of either the left or right visual field. The lack of spatial awareness in one field is produced by the person's predilection to focal stimuli (e.g. something that catches the individual's attention in the opposite field) and is a function of the parietal and occipital cortices. However, a lack of ambient spatial sensorimotor matching at the preconscious level may be related to the conscious sensory neglect. We have clinically observed that when an individual with a field neglect physically touches or holds an object in the neglected field there is increased awareness of objects in the neglected field. Therefore, our clinical observations suggest that VMS may also reinforce visuo-spatial neglect on the affected side due to the spatial distortion produced by ambient and sensorimotor mismatch causing the shift in visual midline or egocenter. Recognizing that VMS showed statistical significance in favour of shifting in the direction of lean and away from the hemiparetic side, it would appear that VMS may interfere with maximizing rehabilitation potential for weight-bearing and ambulation.

It has been noted that physical and occupational therapists often use mirrors in front of patients in order to provide feedback about postural orientation. The therapist uses the mirror to provide feedback through conscious awareness about body-spatial orientation. However, this is an attempt to provide feedback about position that should have been organized through the feedforward preconscious ambient and sensorimotor match of information which produces a feeling of body position upright against gravity. Frequently, doctors and therapists report that when patients are in front of a mirror they can establish an erect posture, but when the mirror is removed the patient returns to a position of leaning and drifting away from the hemiparetic side. This may indicate that without preconscious spatial orientation by ambient and sensorimotor match to produce feed-forward to the cortices, over-focalization will occur in conjunction with spatial distortion, ultimately interfering with awareness of the complete visuo-spatial field. In turn, yoked prisms have been shown to affect neglect. By rehabilitating the spatial function through yoked prisms, we suggest that realignment of the visual midline in addition to affecting neglect will potentially affect rehabilitation outcome.

While the postural orientation, namely forward, rear, left and right lean, can be measure visually. Such visual methods are somewhat subjective and provide good estimates at best. Also, to make such visual measurements requires skill and training. To overcome these shortcomings, the present invention incorporates weight-bearing pressure sensitive walk plates 6 under the tread 4 and/or overhead weight supporting members 8 in a treadmill 2 as in FIG. 2 to evaluate weight-bearing pressure in the right, left, forward and rear directions. This will provide a quantitative means to directly measure the shift in weight bearing in lateral as well as anterior-posterior axes. Yoked prisms can then be incorporated to affect the VMS produced by the CVA. The pressure sensitive plates 6 and/or overhead weight supporting members 8 can be used to quantitatively measure the effect of realigning the visual midline thereby affecting posture and balance in a dynamic environment. From the weight bearing pressure measurements, the lean and direction of the lean can be determined. In other words, the x, y, z and r discussed above with relation to Equation 1 can be determined and easily evaluated by an analyzing means 10 utilizing the Equation 1 above. From these values the number of dioptres of the prism can be determined. Therefore, the number of corrective dioptres for the prism can be directly or indirectly determined from the weight bearing pressure measurements.

The direction of force will be done by determining the direction of lean in a 360 degree circle. With the person facing forward the 0 (zero) or point of 360 degrees is at the person's right shoulder. Directly on the midline is 90 degrees; on the left shoulder is 180 degrees and behind and on midline is 270 degrees. If the person is leaning to the left the sensors will register it at 180 degrees (direction of lean).

The 360 degree circle corresponds to the vertical plane of the glasses. 0 (zero) degrees is to the right; 90 degrees is straight up; 180 degrees is to the left; 270 degrees is straight down; and so on.

For a person leaning to the left, a prism will be positioned with base or thick end directly opposite of the lean (base at 0 (zero) or 360 degrees).

For a person leaning forward the base will be placed base down at 270 degrees.

Many persons have a combination of lateral and anterior-posterior shift requiring an oblique angle for the prism placement.

One diopter of prism deviates an image 1 cm at 1 meter. Correspondingly the ambient process does not recognize the image shift but instead moves the person 1 cm opposite the fixation point therefore, the prism will be used to shift the deviation of the "Visual Midline" or egocenter to counter the lean.

It should be apparent to one of ordinary skill that the above described embodiment represents one of a plurality of embodiments which could be created by one of ordinary skill without departing from the spirit and scope of the invention.

TABLE I

Demographic characteristics of experimental and control subjects.

| Characteristic | Post-CVA Group | Control Group |
|---|---|---|
| Mean Age (years) | 68 SD 6.75 | 63 SD 6.12 |
| Age Range | 56-75 | 52-68 |
| Right CVA | 17 | N/A |
| Left CVA | 13 | N/A |
| Female | 15 | 12 |
| Male | 15 | 18 |

TABLE II

Shifts in visual midline for all subjects.

| Characteristics | Positive VMS Trials | Negative VMS Trials | Right Shift Trials | Left Shift Trials | No Shift Trials | P-value | 95% CI |
|---|---|---|---|---|---|---|---|
| Right CVA | 27 | 7 | N/A | N/A | 0 | <0.001 | 0.66-0.93 |
| Left CVA | 20 | 6 | N/A | N/A | 0 | 0.001 | 0.61-0.93 |
| Control | N/A | N/A | 4 | 1 | 55 | 0.31 | −0.031-0.098 |

TABLE III

Modification of VMS using yoked prisms.

| Characteristics | Positive Shift Trials with Base-Left Yoked Prisms | Positive Shift Trials with Base-Right Yoked Prisms | Left Shift with Base-Left Yoked Prisms | Right Shift with Base-Right Yoked Prisms | P-value | 95% CI |
|---|---|---|---|---|---|---|
| Right CVA | 5 | 25 | N/A | N/A | <0.001 | 0.73-0.97 |
| Left CVA | 20 | 6 | N/A | N/A | 0.001 | 0.069-0.39 |
| Control | N/A | N/A | 27 | 26 | N/A | N/A |

TABLE IV

Direction of lean or drift while ambulating.

| Characteristics | Positive Lean/Drift | Negative Lean/Drift | Right Lean/Drift | Left Lean/Drift | No Lean/Drift | P-value | 95% CI |
|---|---|---|---|---|---|---|---|
| Right CVA | 16 | 1 | N/A | N/A | 0 | <0.001 | 0.83-1.0 |
| Left CVA | 10 | 3 | N/A | N/A | 0 | 0.02 | 0.54-1.0 |
| Control | N/A | N/A | 2 | 1 | 27 | | |
| Left Lean/Drift | | | | | | 0.31 | −0.031-0.098 |
| Right Lean/Drift | | | | | | 0.14 | −0.023-0.16 |

TABLE V

Effects of yoked prisms on direction of lean or drift while ambulating.

| Characteristics | Positive Lean/Drift with Base-Left Yoked Prisms | Positive Lean/Drift with Base-Right Yoked Prisms | P-value | 95% CI |
|---|---|---|---|---|
| Right CVA* | 3 | 14 | <0.001 | 0.64-1.0 |
| Left CVA* | 11 | 2 | <0.001 | 0.65-1.0 |
| Control** | 13 | 15 | N/A | N/A |

*Positive lean or drift is away from the hemiparesis for CVA subjects.
**Control group subjects show left lean with base left yoked prisms, and right lean with base right yoked prisms

The invention claimed is:

1. A means for analyzing gait and balance to determine visual spatial distortion comprising:
    a treadmill having a movable tread;
    at least a weight bearing sensor for measuring weight bearing pressure in right, left, front and rear directions provided under said movable tread; and
    a means for analyzing lean coupled to output of said weight bearing sensor to determine visual midline shift from equation (1):

$$(x^2+y^2+z^2)/r^2=1 \quad \text{Equation (1)}$$

wherein x, y and z are amount of lean in x, y, and z directions and r is a radius of a physiological egocenter.

2. The means for analyzing gait and balance to determine visual spatial distortion according to claim 1, wherein said weight bearing sensor comprises weight bearing pressure sensitive walking plates.

3. A method of analyzing gait and balance to determine visual spatial distortion, comprising the steps of:
    providing a test subject walking on moving tread of a treadmill;
    measuring weight bearing pressure in right, left, front and rear directions by means of a weight bearing sensor provided under said moving tread; and
    analyzing lean from output of said weight bearing sensor to determine visual midline shift.

4. The method of claim 3 wherein said lean is analyzed from equation (1):

$$(x^2+y^2+z^2)/r^2=1 \quad \text{Equation (1)}$$

wherein x, y and z are amount of lean in x, y, and z directions and r is a radius of a physiological egocenter.

5. The method according to claim 4, further comprising the step of selecting corrective yoked prisms based upon the analyzed lean.

* * * * *